United States Patent [19]

Holtkamp, Sr.

[11] Patent Number: Plant 7,698

[45] Date of Patent: Oct. 29, 1991

[54] AFRICAN VIOLET PLANT NAMED HAITI

[76] Inventor: Reinhold Holtkamp, Sr.,
Blumenstrasse 28, D 4242
Rees-Haffen, Fed. Rep. of Germany

[21] Appl. No.: 565,320

[22] Filed: Aug. 10, 1990

[51] Int. Cl.[5] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner

[57] ABSTRACT

A new and distinct cultivar of African violet named Haiti characterized by its wavy, purple, star-shaped flowers with frilled, white edges; strong, upright flower stems that curve slightly toward the center to form a compact bouquet above the leaves; dark green, wavy and serrated leaves; profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Haiti.

The new cultivar was referred to during the breeding and selection process by the designation 815/8 and is a product of a planned breeding program. The new cultivar was originated from a cross made by me in the controlled breeding program in Haffen, Federal Republic of Germany. The female, or seed parent was a cultivar designated 2820. The male, or pollen parent was a cultivar designated 72/94 bl. si. va.

Haiti was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Haiti has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Haiti, which in combination distinguish this African violet as a new and distinct cultivar:

(1) Strong, upright flower stems curving slightly toward the center.
(2) Wavy, purple, star-shaped flowers with frilled white edges.
(3) Profuse flowering.
(4) Each plant carries 7–9 and more upright flower stems each of which carries 7–8 and more flowers.
(5) Long lasting, non-dropping flowers.
(6) Vigorous grower.
(7) Plant saleable 10 to 11 weeks after potting.
(8) Seed capsules push slightly through.
(9) Wavy, dark green, oval to spear-shaped leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Color Chart (RHS), except where general colors of ordinary significance are referred to. Color values were taken under natural sunlight conditions at approximately 12 a.m. in Nashville, Tenn.

Botanical classification: *Saintpaulia ionantha,* Ramat., c.v. Haiti.

Parentage:
- *Male parent.*—2820.
- *Female parent.*—792/94 bl. si. va.

Propagation: The new cultivar holds its distinguishing characteristics through successive propagations by leaf cuttings.

Plant: From 8 cm to 11 cm tall when grown in pots, and approximately 25–28 cm in diameter when fully grown.

Leaves:
- *General form.*—Oval to spear-shaped.
- *Diameter.*—60–70 mm wide and 70–75 mm long.
- *Texture.*—Leatherlike.
- *Aspect.*—Wavy, serrated, hairy, slightly shiny.
- *Veins.*—Upperside; visible; underside: well pronounced, light green, shiny.
- *Color (upperside).*—Yellow-Green Group 147 A and somewhat darker.
- *Color (underside).*—Greyed-Purple Group 186 A.
- *Petiole.*—Strong upright, green with purplish brown touch, hairy.

Flowers:
- *Buds.13* Bell-shaped, 7–9 mm just before opening, purple, white edges already visible.
- *Sepals.13* Five (5). Color: Green with purplish brown touch.
- *Calyx:* Shape: Funnel-shaped. Aspect: Spear-shaped, hairy.
- *Peduncle.*—Character: Strong upright, hairy. Color: Green with purplish brown touch.

Individual flowers:

*Size.*—40–45 mm.

*Shape.*—Star-shaped.

*Color (upperside).*—Purple-Violet Group 82 A to B, white edges. Under cooler temperatures and more intensive lighting, the purple color tends to intensify.

*Color (underside).*—Violet Group 87 B.

*Borne.*—Each flower stem carries 7–8 and more flowers on strong, upright peduncles that are free standing above the leaves, thereby forming a compact bouquet.

*Flowering habit.13* Flowers 10–11 weeks after potting.

Reproductive organs:

*Stamens.*—Five (5). Anthers: 5 composed of 10 anther cells, seed capsule pushes slightly through.

*Filaments.*—Yellowish green with purple on edges, 3–4 mm long.

*Pollen color.*—Yellow Group 7 A.

*Styles.*—7–8 mm long, purple, base of ovary light green and hairy.

Roots: Normally developed, white when young, turning slightly brownish when older.

Disease resistance: Up to date, Haiti has shown very good resistance to all major violet diseases.

General observations: Haiti is an attractive, vigorous and compact grower with wavy, star-shaped, purple flowers having frilled, white edges. A nice bouquet of flowers free standing above the leaves develops after approximately 10–11 weeks. Each of the 7–9 and more strong flower stems carries 7–8 and more wavy flowers with frilled edges. Occasionally, one to two additional very small petals may develop in the center. The flowers are long-lasting and non-dropping and the seed capsules push slightly through. The leaves are dark green, serrated and wavy.

I claim:

1. A new and distinct cultivar of African violet named Haiti, as described and illustrated, and particularly characterized by its wavy, purple, star-shaped flowers with frilled, white edges; strong, upright flower stems that curve slightly toward the center to form a compact bouquet above the leaves; dark green, wavy and serrated leaves; profuse flowering, vigorous growth habit, flowering 10–11 weeks after potting, and its long lasting and non-dropping flowers.

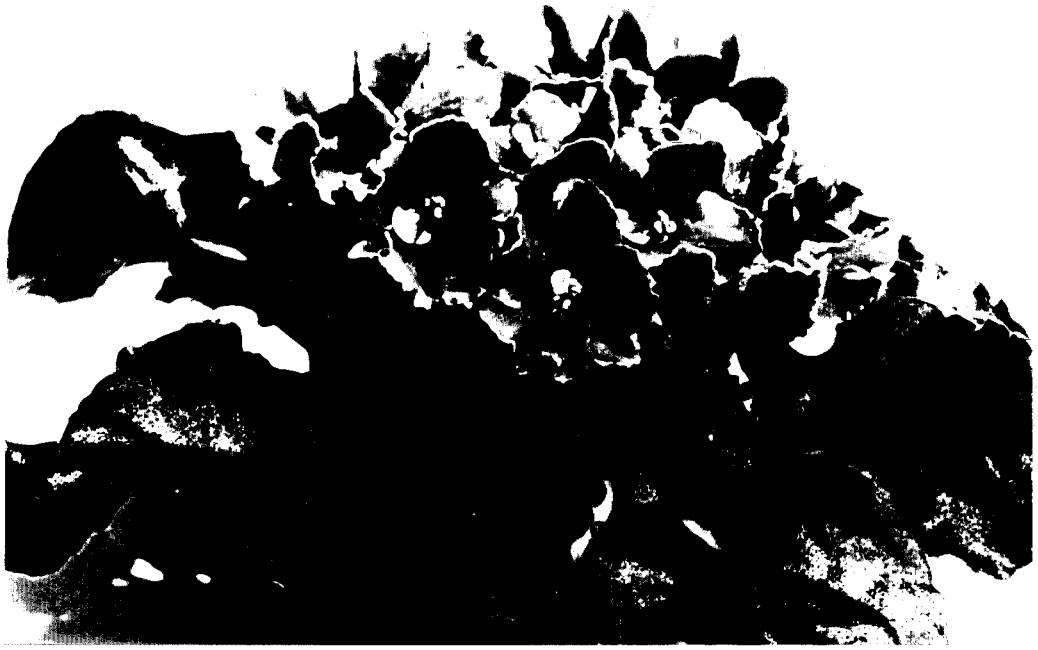

* * * * *